United States Patent [19]
Selga et al.

[11] Patent Number: 5,998,335
[45] Date of Patent: Dec. 7, 1999

[54] HERBICIDAL COMPOSITION AND METHOD

[76] Inventors: John Selga; Wayne Andrew Kiely, both of Jury Rd., Monash, S. Australia, Australia

[21] Appl. No.: 09/068,355
[22] PCT Filed: Nov. 6, 1995
[86] PCT No.: PCT/AU95/00739
§ 371 Date: May 6, 1998
§ 102(e) Date: May 6, 1998
[87] PCT Pub. No.: WO97/16975
PCT Pub. Date: May 15, 1997

[51] Int. Cl.$^6$ .............................. A01N 31/06; A01N 65/00
[52] U.S. Cl. ............................................................ 504/353
[58] Field of Search ............................................. 504/353

[56] References Cited

U.S. PATENT DOCUMENTS

| | | | |
|---|---|---|---|
| 2,512,044 | 6/1950 | Swaney et al. | 71/2.7 |
| 3,592,910 | 7/1971 | Clark et al. | 424/300 |
| 4,587,123 | 5/1986 | Price | 424/195.1 |
| 5,035,741 | 7/1991 | Puritch et al. | 71/113 |
| 5,407,899 | 4/1995 | Howell | 504/152 |

FOREIGN PATENT DOCUMENTS

| | | |
|---|---|---|
| 19517/88 | 5/1991 | Australia . |
| 17882/95 | 7/1995 | Australia . |
| 17959/95 | 11/1995 | Australia . |
| 504333 | 7/1930 | Germany . |
| WO 93/19598 | 10/1993 | WIPO . |

OTHER PUBLICATIONS

Putnam, A.R., "Allelopathic Chemicals, Nature's Herbicides in Action," *Chemical and Engineering News*, Apr. 4, 1983, pp. 34–45, 61.

Vaughn, S.F. and Spencer, G.F., "Volatile Monoterpenes as Potential Parent Structures for New Herbicides," *Weed Science*, Jan.–Mar. 1993, pp. 114–119, vol. 41.

Williamson, G.B., et al., "Chemical Inhibition of Fire–Prone Grasses by Fire–Sensitive Shrub, *Conradina canescens*," *Journal of Chemical Ecology*, 1989, pp. 1567–1577, vol. 15, No. 5.

Weaver, T. and Kish, L., "Allelopathic Potential of Terpene Secreting (Aromatic) Plants," *Proc. Mont. Acad. Sci.*, 1982, pp. 51–56, vol. 41.

Del Moral, R. and Muller, C.H., "The Allelopathic Effects of *Eucalyptus camaldulensis*," *The American Midland Naturalist*, Jan., Apr. 1970, pp. 254–282, vol. 83.

Klingman, G.C., Chapter 14: "Other Organic Herbicides," *Weed Control: As a Science*, Sep. 1963, pp. 208–225, John Wiley and Sons, Inc., USA.

Kirk–Othmer, "Terpenoids," *Encyclopedia of Chemical Technology*, pp. 709–712, vol. 22, Third Edition, John Wiley and Sons, New York 1985.

Derwent abstract Accession No. 90–284353, Class C02, EP 388164, (Du Pont De Nemours Co.), Sep. 19, 1990.

Derwent abstract Accession No. 87–286557, Class C02, (Shell Int. Res. Miy BV), Oct. 14, 1987.

Derwent abstract Accession No. 88–216573, Class C02 (C03), JP A 63–152303, (Mitsubishi Petroch KK), Jun. 24, 1988.

Derwent abstract Accession No. 88–231637, Class C02 (C03), JP A 63–165301, (Shell Kagaku KK), Jul. 8, 1988.

May, J.W. et al., "SD 95481 A Versatile New Herbicide with Wide Spectrum Crop Use," Proc. Br. Crop. Prot. Conf., 1985, pp. 265–270, vol. 12.

Al Saadawi, I.S. et al., "Allelopathic Effects of *Citrus aurantium* L. II. Isolation, Characterization, and Biological Activities of Phytotoxins," *Journal of Chemical Ecology*, 1985, pp. 1527–1534, vol. 11, No. 11.

Muller, W.H. and Muller, C.H., "Volatile Growth Inhibitors Produced by *Salvia* Species," Bulletin of The Torrey Botanical Club 1964.

Derwent abstract Accession No. 88–119336, Class C02, WO–A–8802598, (Du Pont De Nemours Co.), Apr. 21, 1988.

Fischer, N.H., Chapter 12: "The Function of Mono and Sesquiterpenes as Plant Germination and Growth Regulators," *The Science of Allelopathy*, 1986, pp. 203–218, John Wiley and Sons, New York.

Elakovich, S.D., Chapter 16: "Terpenoids as Models for New Agrochemicals," *Biologically Active Natural Products: Potential Use in Agriculture*, American Chemical Society symposium series, 1988, pp. 250–261, H.G. Cutler Editor, Washington, DC.

*The Merck Index*, 1983, Monographs 3840, 5321, 6658, 6692, 7319, 7320, 7321, Merck & Co., Inc., Rahway, N.J., USA.

Derwent abstract Accession No. 91–152274, Class C03, (Sanyo Chem. Ind. Ltd.), Apr. 11, 1991.

Derwent abstract Accession No. 93–299519, Class C03, (Solar Japan KK), Aug. 24, 1993.

Haag, K.H., "Effects of Herbicide Application on Mortality and Dispersive Behavior of the Water Hyacinth Weevils, *Neochetina eichhorniae* and *Neochetina bruchi* (Coleoptera: Curculionidae)," *Environmental Entomology*, 1986, pp. 1192–1198, vol. 15, No. 6.

Riken Vitamin Co. Ltd. JPO Abstract of JP 03–223428, Feb. 1993.

Primary Examiner—S. Mark Clardy
Attorney, Agent, or Firm—Brown Martin Haller & McClain LLP

[57] ABSTRACT

A knock-down herbicidal composition consisting essentially of the combination of (a) pine oil, and (b) tea tree oil or eucalyptus oil.

5 Claims, No Drawings

HERBICIDAL COMPOSITION AND METHOD

This application has been filed under 35 U.S.C. 371 as the national stage of international application PCT/AU95/00739, filed Nov. 6, 1995.

BACKGROUND TO THE INVENTION

The present invention relates to a herbicidal composition having, as an active ingredient, a terpene compound, a terpene derivative, or an essential oil comprising a terpene compound or derivative. In particular, the herbicidal composition will comprise a pine oil, dipentene, pinene, a pine alcohol or a terpene compound or derivative derived from pine oil. A citrus oil or a terpene compound derived from citrus oil, e.g. limonene (1-methyl-4-(1-methylethenyl)-cyclohexene), may also be used.

Many herbicidal compositions presently on the market are highly toxic to humans and domestic animals. A herbicide having lower toxicity is desirable, particularly for use by the home gardener.

The active ingredient of the present herbicidal compositions has the advantage of being an environmentally friendly, natural product, which is unlikely to cause environmental pollution or create toxicity problems for humans or domestic animals.

SUMMARY OF THE INVENTION

The present invention provides a herbicidal composition, having as an active ingredient a terpene compound or derivative, which may be either naturally occurring or synthetic. (Natural pine oil, for example, is virtually unobtainable.)

Although the terpene compounds or derivatives are believed to be the active ingredients of the herbicidal compositions, the same herbicidal effect is found using "whole" essential oils, such as pine oils and citrus oils, comprising such terpene compounds or derivatives.

The addition of other essential or natural oils can enhance the activity of the preparation.

In a further aspect, the invention provides a method for controlling unwanted plant growth, wherein a terpene compound or derivative, an essential oil comprising a terpene compound or derivative, or a herbicidal composition having, as an active ingredient, a terpene compound or derivative or an essential oil comprising a terpene compound or derivative is applied to the unwanted plant or plants.

DETAILED DESCRIPTION OF THE INVENTION

The active ingredient of the present herbicidal compositions is a naturally occurring or synthetic terpene (e.g. dipentene, limonene or pinene) or terpene derivative (e.g. terpineol or a pine alcohol), or an essential oil (e.g. a pine or citrus oil), in either pure or diluted form. Examples of suitable citrus oils are orange, lemon, grapefruit, mandarin, tangerine or tangelo oil, and in particular orange oil.

Although the preferred active ingredient is a pine oil or a terpene compound or derivative derived from pine oil, other essential oils, terpenes and terpene derivatives may also be effective, e.g. citrus oils, citrus oil derivatives, terpenes or terpene derivatives derived from citrus oils, tea tree oil (Oil of Melaleuca) and eucalyptus oil. The major terpene derivative present in pine oil is terpineol. As with pine oil, the major terpene derivatives present in tea tree oil and eucalyptus oil are alcohol compounds, being terpinen-4-ol and cineole (eucalyptol) respectively.

In particular, dipentene, which is a synthetic derivative of pine oil predominantly comprising d,l-limonene, has been found to be effective.

In a preferred embodiment, the major active component of the herbicidal compositions is pine oil, a pine alcohol, pinene, dipentene or d-limonene. The last-mentioned compound is found in many essential oils and is the major active component of citrus oils.

l-Limonene has also been trialled, and appears to be as herbicidally-effective as d-limonene.

Tea tree and eucalyptus oils display very high herbicidal activity, but are currently high cost materials available in limited volumes. Therefore, until prices drop with increased world production, it is preferred that these oils be incorporated in the herbicidal compositions of the present invention as minor additives. Both tea tree oil and eucalyptus oil were found to enhance the herbicidal activity of an emulsion of pine oil when added at concentrations as low as 1.5% by volume. If appears that they have a synergistic effect when added to pine oil.

The herbicidal compositions of the present invention are non-selective, non-systemic herbicides, which are effective against almost any vegetation, and specifically against common crop and garden weeds, both annual and perennial. They are "knock-down" herbicides, which must be sprayed over a substantial portion of the above-ground part of the plant, in order to have effect. Conveniently, the herbicides are applied as a fine droplet spray. The non-systemic nature of the present herbicidal compositions is a considerable advantage to the home gardener, as spray drift is unlikely to cause problems. If a small amount of the herbicidal composition lands on a wanted plant, that plant is unlikely to be killed or badly damaged. A further consequence of the non-systemic nature of the herbicide is that the weed does not have to be in an active growth stage, in order for the herbicide to be effective. The herbicide will even work on dormant plants. Furthermore, the herbicidal effect is not dependent on weather conditions, or adversely affected by moisture. Rain or irrigation after application of the herbicidal composition to unwanted plant growth does not destroy the herbicidal effect.

Most terpene compounds, terpene derivatives and essential oils have the advantage of being considerably safer than common agricultural chemicals, such as conventional herbicides. Terpene compounds and derivatives have been widely used, for some years, in medicines, cosmetics and foodstuffs, and thus their safety has been established. Accordingly, the terpene compounds, terpene derivatives and essential oils will also be non-environmentally-polluting and non-toxic to domestic animals. In particular, the herbicides of the present invention are non-residual, when purified pine oil or citrus terpenes are used as the active ingredient.

In use, the terpene, terpene derivative or essential oil may be applied to unwanted plant growth either by itself, or in the form of a conventional herbicidal composition. For example, the active ingredient of the present invention may be mixed with a carrier or diluent to form an easily applied formulation, which may be diluted according to the particular application.

Examples of herbicidal formulations include sprays, liquids, wettable powders, oily solutions, emulsions, dusts, granules, fumigants etc. Application may be by spraying or by means of a "touch" applicator, using a wick assembly.

In particular, emulsions comprising water, an essential oil and a commercial food grade emulsifying agent have been trialled. Whilst the amount of active ingredient is lower in such systems, trials conducted with limonene suggest that volatility is lowered, thereby prolonging contact between the weed and the herbicide. This effect offsets the reduction in active ingredient content.

Alternatively, terpenes, terpene derivatives or essential oils may be blended with other, cheaper, and somewhat less volatile oils to form effective herbicides. For example, various natural oils (such as cottonseed oil, soybean oil, rapeseed oil, sunflower oil, safflower oil, olive oil, coconut oil, coconut milk, corn oil, grape seed oil and peanut oil) have been tested, and found to lack significant herbicidal activity. Nevertheless, they can be blended with the herbicidally-effective essential oils of the present invention to form effective herbicidal compositions.

Because of their environmentally friendly nature and low toxicity, the herbicidal compositions of the present invention will be of particular benefit to the home gardener. However, they may also be used in large-scale agriculture.

In a preferred embodiment, the active ingredient is d-limonene derived from a citrus oil, e.g. orange oil. The fraction comprising d-limonene is separated off by vacuum distillation, or any other conventional separation process. d-Limonene is volatile, and is separated off in the distillate. The distillate is a highly concentrated composition of the terpene compound, comprising about 95–96% by weight of d-limonene and about 4–5% by weight of other components. This distillate may be utilised directly as the herbicidal composition of the present invention.

It should be noted that, although d-limonene is believed to be the active ingredient of this herbicidal composition, other components present in the distillate may also have a herbicidal effect. Furthermore, it may be possible to use unrefined citrus oil, instead of the vacuum distillate. However, vacuum distillation (or other separation process, such as steam distillation (azeotroping), solvent extraction, supercritical extraction etc.) has the advantage of separating the herbicidally active ingredient from flavour components of the citrus oil. The flavour components then form a valuable by-product, which can be utilised in e.g. foodstuffs or pharmaceutical compositions.

The invention will now be further described with respect to the following Examples, which are illustrative but not restrictive of the present invention.

EXAMPLE 1 d-Limonene, which can occur at levels of up to 95% in citrus oils, was distilled from Australian orange oil by vacuum distillation.

The d-limonene used in this trial was approximately 96% pure but, as with all commercially prepared citrus terpenes, contained various other natural compounds distilled in the "cut". The main ones were:

Ethanol
alpha-Pinene
Sabinene
Myrcene
Octanal
gamma-Terpinene
Linalool
Citronellal
alpha-Terpinene
Decanal
Nerol
Neral
Geraniol
Geranial
Dodecanol
Dodecanal.

The d-limonene fraction was applied to vegetation as a fine droplet spray.

Knockdown trials were carried out on vegetation growing in heavier (more clay) soils and lighter (more sand) soils. No significant differences in timing or effect were noted.

Knockdown trials were also carried out during different seasons and at different growth stages of the vegetation. Again, no significant differences in timing or effect were noted.

The d-limonene fraction was found to be non-selective and effective against most common vegetation types, including annual and perennial weeds (see Table 1 below). Most vegetation showed visible signs of stress (e.g. wilting or browning) within 2 to 24 hours of application of the herbicide.

Further trials were carried out, as described in Examples 2 to 4 below. The results of these trials are shown in Table 1

EXAMPLE 2 d-Limonene, which was prepared by the distillation process of Example 1, was formulated as an emulsified mixture of 60% d-limonene with water and commercial emulsifier. Its herbicidal efficacy was tested, using the procedures described in Example 1.

EXAMPLE 3

Similar tests were carried out with dipentene (d,l-limonene) derived from pine oil (a commercial sample, used "neat").

EXAMPLE 4

A commercial sample of pine oil, used "neat", was tested.

TABLE 1

HERBICIDE KNOCKDOWN TRIALS

| VEGETATION | 96% d-LIMONENE | | | 60% d-LIMONENE EMULSION | | | DIPENTENE (d,1-LIMONENE) | | | PINE OIL | | |
|---|---|---|---|---|---|---|---|---|---|---|---|---|
| | A | B | C | A | B | C | A | B | C | A | B | C |
| Soursob (Oxalis pes-caprae) | 1 | 12 | NO | 1 | 18 | NO | 1 | 12 | NO | 1 | 12 | NO |
| Caltrop (Tribulus terrestris) | 2 | 12 | NO | 3 | 18 | NO | 2 | 12 | NO | 2 | 12 | NO |
| Ryegrass (Lolium rigidum) | 2 | 12 | NO | 2 | 18 | NO | 2 | 12 | NO | 1 | 6 | NO |
| Saffron Thistle (Carthamus lanatus) | 24 | 48 | NO | 36 | 48 | NO | 24 | 48 | NO | 18 | 48 | NO |
| Wild Turnip - Young Plant (Brassica tournefortii) - Mature Plant | 12 / 18 | 24 / 36 | NO / OCCAS. | 12 / 24 | 24 / 48 | NO / OCCAS. | 12 / 18 | 24 / 36 | NO / OCCAS. | 12 / 12 | 18 / 36 | NO / OCCAS. |
| Couch Grass (Cynodon dactylon) | 6 | 48 | OCCAS. | 6 | 48 | OCCAS. | 6 | 48 | OCCAS. | 6 | 36 | OCCAS. |

NOTES:
A = Time to first visible stress (Hrs)
B = Plant knockdown (Hrs)
C = Regrowth (after 2 weeks) OCCAS. = Occasional
Application: Household style trigger spray (Calmar Model TS-800-1) with 500 ml reservoir - spray nozzle setting (mist).
Rate: Aim to achieve 60–80% coverage of vegetation.
Soil: Sandy Loam.

EXAMPLE 5

A pine-based emulsion (approx. 30% v/v pine oil in water, with a commercial emulsifying agent) was trialled for herbicidal activity.

The pine-based emulsion was shaken well and test sprayed on 19/07/95 between 9–10am with the temperature below 12° C. The viscosity of this formulation did not allow it to spray well, resulting in only partial coverage. Spray drift was low. Within 8 hours most sprayed plants showed contact necrosis. Where reasonable coverage had been achieved, good kill rates followed. For wild oats and milk thistle, partial coverage allowed recovery by tillering or tip growth respectively. Woody Eucalyptus stem tissue also resprouted.

Results after 10 days were as follows:

Grass, wild oats—rapid dessication of fine leaves but larger leaves more resilient. Growth continued from protected apex.

Gazania—reasonable kill rate with long-lasting effect.

Sour sob—rapid above ground foliar kill, effect on bulb unknown.

Blackwood Wattle—rapid necrosis and permanent kill of foliage and stem to 5mm diameter.

Casuarina—no initial effect; surface dull at 10 days; dead in contact area after 1 month.

Saltbush, Rhagodia—rapid necrosis of foliage and stem tissue with permanent kill.

Melaleuca stypheloides—rapid necrosis and permanent kill of foliage and stems<5 mm diameter.

Wireweed—rapid necrosis of foliage and stem tissue with permanent kill.

River red gum—rapid necrosis of mature and young foliage, but stems later resprouted. Eucalyptus stem tissue of 5 mm diameter and larger resprouted after 2 months.

Other test plants which showed a rapid spray contact kill rate were: Nigella, Plantago, Senecio, Salvation Jane, Medic and Osteospermum. Young Valerian plants died, but older plants with succulent roots only suffered contact damage to foliage. Thistles showed contact damage, but growing tips were not damaged enough to kill the plants. Their growing tips continued to shoot and flower.

Accordingly, the pine-based emulsion was herbicidally effective against numerous species of weeds, some with known glyphosate resistance and some being of a "woody" nature.

While the present invention has been described in terms of preferred embodiments in order to facilitate better understanding of the invention, it should be appreciated that various modifications can be made without departing from the principles of the invention. Therefore, the invention should be understood to include all such modifications within its scope.

We claim:

1. A "knock-down" herbicidal composition effective against mature weeds having, as its sole active ingredient, a synergistic combination of (a) pine oil and (b) tea tree oil or eucalyptus oil.

2. A method for controlling the growth of mature, unwanted plant(s), wherein a pine oil or terpineol, or a herbicidal composition having, as its sole active ingredient, a pine oil or terpineol, is applied to the unwanted plant or plants.

3. A method according to claim 2, wherein a pine oil, or a herbicidal composition having, as its sole active ingredient, a pine oil, is applied to the unwanted plant or plants.

4. A method according to claim 2, wherein terpineol, or a herbicidal composition having; as its sole active ingredient, terpineol, is applied to the unwanted plant or plants.

5. A method for controlling the growth of mature, unwanted plant(s), wherein a synergistic combination of (a) pine oil and (b) tea tree oil or eucalyptus oil, or a herbicidal composition having, as its sole active ingredient, a synergistic combination of (a) pine oil and (b) tea tree oil or eucalyptus oil, is applied to the unwanted plant or plants.

* * * * *